US012765932B2

(12) United States Patent
Badcott et al.

(10) Patent No.: US 12,765,932 B2
(45) Date of Patent: Oct. 20, 2026

(54) ORTHOPAEDIC CEMENT REMOVAL TOOLS

(71) Applicant: RADLEY SCIENTIFIC LIMITED, South Devon (GB)

(72) Inventors: Sean Martin Badcott, Devon (GB); Stephen Michael Radley Young, Devon (GB)

(73) Assignee: RADLEY SCIENTIFIC LIMITED, South Devon (GB)

( * ) Notice: Subject to any disclaimer, the term of this patent is extended or adjusted under 35 U.S.C. 154(b) by 358 days.

(21) Appl. No.: 18/006,792

(22) PCT Filed: Jul. 26, 2021

(86) PCT No.: PCT/GB2021/000085
§ 371 (c)(1),
(2) Date: Jan. 25, 2023

(87) PCT Pub. No.: WO2022/023689
PCT Pub. Date: Feb. 3, 2022

(65) Prior Publication Data
US 2023/0293212 A1 Sep. 21, 2023

(30) Foreign Application Priority Data
Jul. 27, 2020 (GB) ...................................... 2011627

(51) Int. Cl.
*A61B 17/32* (2006.01)
*A61B 17/88* (2006.01)

(52) U.S. Cl.
CPC .................... *A61B 17/8847* (2013.01); *A61B 2017/320098* (2017.08)

(58) Field of Classification Search
CPC ................ A61B 17/8847; A61B 2017/320068
See application file for complete search history.

(56) References Cited

U.S. PATENT DOCUMENTS

| | | | |
|---|---|---|---|
| 4,750,488 | A | 6/1988 | Wuchinich et al. |
| 5,536,266 | A | 7/1996 | Young et al. |

(Continued)

FOREIGN PATENT DOCUMENTS

| | | | |
|---|---|---|---|
| JP | 3225095 U | 2/2020 | |
| WO | 1999044514 A1 | 9/1999 | |
| WO | 2020065245 A | 4/2020 | |

OTHER PUBLICATIONS

International Search Report and Written Opinion for PCT/GB2021/000085 completed Nov. 5, 2021, 12 pgs.

(Continued)

*Primary Examiner* — Nicholas W Woodall
(74) *Attorney, Agent, or Firm* — HESLIN ROTHENBERG FARLEY & MESITI P.C.

(57) ABSTRACT

An ultrasonically-vibratable surgical tool for cement removal in revision arthroplasty, comprises an elongate solid shaft. This can be mounted at its proximal end to a source of ultrasonic vibrations, so that the shaft acts as a waveguide for propagation of the ultrasonic vibrations. The shaft has at its distal end an operative head to act on the cement. An intermediate portion of the elongate shaft is provided with at least one row of dimples extending helically along and around that portion of the elongate shaft. Each dimple is separate from each adjacent dimple. The dimples may have a shallow part-spherical profile.

22 Claims, 3 Drawing Sheets

(56) References Cited

U.S. PATENT DOCUMENTS

| | | | | |
|---|---|---|---|---|
| 5,697,545 | A | 12/1997 | Jennings et al. | |
| 5,891,149 | A | 4/1999 | Young et al. | |
| 6,425,906 | B1 | 7/2002 | Young et al. | |
| 6,955,680 | B2 * | 10/2005 | Satou | B06B 3/00 606/169 |
| 7,651,490 | B2 * | 1/2010 | Boukhny | A61F 9/00745 606/1 |
| D893,029 | S | 8/2020 | Qun | |
| 2001/0047166 | A1 | 11/2001 | Wuchinich | |
| 2005/0277869 | A1 | 12/2005 | Boukhny | |
| 2006/0004396 | A1 * | 1/2006 | Easley | A61B 17/1659 606/169 |
| 2008/0058585 | A1 | 3/2008 | Novak et al. | |
| 2010/0100139 | A1 | 4/2010 | Young | |
| 2011/0278988 | A1 * | 11/2011 | Young | B06B 3/00 310/328 |
| 2013/0184711 | A1 | 7/2013 | Rad | |
| 2014/0265024 | A1 * | 9/2014 | Quearry | A61B 8/0841 264/293 |
| 2016/0302816 | A1 * | 10/2016 | Clayton | G06F 30/23 |
| 2017/0014151 | A1 | 1/2017 | Voic | |
| 2017/0143398 | A1 * | 5/2017 | Young | A61B 17/8847 |
| 2018/0103976 | A1 * | 4/2018 | Heavey | A61B 17/320068 |
| 2018/0368877 | A1 | 12/2018 | Downey | |
| 2019/0365409 | A1 * | 12/2019 | Badcott | A61B 17/320068 |
| 2021/0338297 | A1 * | 11/2021 | Young | A61B 17/1604 |

OTHER PUBLICATIONS

Examination Report of the UK Intellectual Property Office for GB 2601592, mailed Jul. 16, 2024.

Office Action ofthe Japanese Patent Office for JP 2023-535810, mailed Apr. 1, 2025.

Office Action ofthe European Patent Office for EP 4188248 A, mailed Oct. 30, 2024.

Examination Report of the IP Australia Office for AU 2021316786, mailed Mar. 18, 2026.

Office Action ofthe China National Intellectual Property Administration, for CN 116322540, mailed Nov. 6, 2025.

* cited by examiner

ORTHOPAEDIC CEMENT REMOVAL TOOLS

CROSS REFERENCE TO RELATED APPLICATIONS

This application is a U.S. National Phase filing under 35 U.S.C. § 371 of International Application PCT/GB2021/000085, filed Jul. 26, 2021, and published as WO 2022/023689 A1 on Feb. 3, 2022. PCT/GB2021/000085 claims priority from British application number 2011627.3, filed Jul. 27, 2020. The entire contents of each of these prior applications are hereby incorporated herein by reference.

The present invention relates to surgical tools for the removal of surgical cement during the revision of orthopaedic implants (revision arthroplasty). More particularly but not exclusively, it relates to ultrasonically-vibratable tools for the removal from a bone cavity of surgical cement associated with an orthopaedic implant, particularly after removal of the implant. The present invention further relates to a method for carrying out revision arthroplasty or similar procedures, employing such tools.

Orthopaedic implants, such as hip joint replacements, are very often held in place by at least one component of the implant having an elongate, tapering shaft extending therefrom into a lumen of an adjacent hollow bone, such as a femur for a hip joint. Sometimes the shaft is secured in place by cancellous bone ingrowing from the walls of the bone. However, surgical cement based on poly(methyl methacrylate), often referred to PMMA cement, is more frequently used to anchor the implant.

Such implants may be rated for a lifetime of up to 20 years. However, nowadays the recipients of orthopaedic implants routinely live for longer than 20 years after the procedure. As life expectancies increase, so does the probability of failure of the implant, necessitating its revision. "Failure" may comprise failure of the metal of the implant itself, or localised failure of the cement holding the implant in place, such that the implant comes loose. During revision, the implant or its fragments are first extracted from the bone cavity, and then the cement that remains in the cavity. Not just the bulk cement, but any significant traces of residual cement must be removed. Only then is the implantation of a new prosthesis with fresh cement permissible, as residual cement can lead to inferior adhesion or may act as a defect from which failures of the cement may propagate.

The original surgical approach to removal of residual hardened PMMA cement was literally to chisel it out of the lumen of the bone. This was a slow, inefficient and tiring procedure for the surgeon, usually taking hours to complete. There was always a risk of chisel damage to the bone adjacent the cement, particularly with elderly patients having more brittle bones. Such a prolonged procedure under general anaesthesia would also represent a significant risk for the patient.

A significant step forward came when it was discovered that application of ultrasonically-vibrated tools led to rapid softening and even flow of the PMMA cement, allowing for much easier removal. The procedure may even be carried out using less invasive approaches, such as laparoscopy. The resulting shorter procedure was not only preferable for the surgeon, but also reduced the risks associated with prolonged anaesthesia. Examples of such tools were, for example, disclosed in European Patent No EP0599950.

This approach has been widely adopted since its introduction in the 1990s, but there will always be a demand for improvements for such major surgical procedures. For example, some of the early ultrasonically-vibrated tools could still cause local damage to bone, if activated when the operative distal tip is aligned towards the bone.

Meanwhile, significant effort has been put into exploring the effects of different vibrational modes of ultrasound. Conventionally, longitudinal-mode vibrations have been used, as they are easiest to generate. However, in the area of soft-tissue surgery, significant advantages have been found for torsional-mode ultrasonically-vibrated apparatus compared with longitudinal-mode ultrasonically-vibrated apparatus. These surgical tools for soft-tissue cutting and cauterising are of no use in arthroplasty, but it has led to advances in the technology of torsional-mode ultrasonic vibrations that speculatively might have benefits in orthopaedic surgery, too.

A particular issue with the original ultrasonically-vibrated tools for revision arthroplasty was that softened cement could readily escape removal by hardening again before collection, or softened cement could harden again after collection and adhere inconveniently to the tool itself, becoming hard to remove and possibly even harming the function of the tool.

It is hence an object of the present invention to provide improved ultrasonically-vibratable surgical tools that obviate the drawbacks of existing tools for orthopaedic procedures such as cement removal in revision arthroplasty, so as to permit more rapid and convenient extraction of residual surgical cement from within hollow bones.

According to a first aspect of the present invention, there is provided an ultrasonically-vibratable surgical tool adapted for cement removal in revision arthroplasty, comprising elongate solid shaft means, mountable at a proximal end to a source of ultrasonic vibrations, so as to act as a waveguide for propagation of said ultrasonic vibrations, and having located adjacent a distal end of the shaft means an operative head adapted to act on the cement, wherein a portion of the elongate shaft means intermediate between said proximal and distal ends is provided with at least one row of recess means extending helically along and around said portion of the elongate shaft means, with each said recess means being separate from each adjacent said recess means.

Preferably, each said recess means extends into the shaft means to a depth of less than half of a maximum width of the recess means.

Advantageously, each said recess means extends into the shaft means to a depth of less than a quarter of said maximum width.

Each said recess means may comprise dimple means formed into a surface of the elongate solid shaft means.

Preferably, each said recess means is identical to each other said recess means.

Preferably, each recess means comprises a circular recess.

Advantageously, each circular recess has a part-spherical profile.

Each said circular recess may have a part-spherical profile shallower than a hemisphere.

Alternatively, each said recess may have a substantially cylindrical form.

A base of each said substantially cylindrical recess may then have a slightly concave profile.

Preferably, the or each of said at least one row of recess means extends for less than an overall length of said portion of the elongate shaft means.

Advantageously, the or each of said at least one row of recess means extends for more than half of the overall length of said portion.

The or each of said at least one row of recess means may extend for less than three-quarters of the overall length of said portion.

Optionally, the or each of said at least one row of recess means may extend for about two-thirds of the overall length of said portion.

Preferably, there are at least two said rows of recess means.

Advantageously, each said row of recess means is substantially identical to each other said row.

Each said recess means may be spaced from each adjacent recess means in the same row by a separation of less than one fifth, optionally less than one tenth, of a maximum diameter of each said recess means.

Each row of said at least two rows of recess means may be spaced from each adjacent row thereof by a separation of at least twice a maximum diameter of the recess means, optionally at least three times said maximum diameter, ideally about four times said maximum diameter.

Preferably, the elongate solid shaft means of the tool comprises at least one frustoconically tapering gain section.

Advantageously, the elongate solid shaft means of the tool comprises two said frustoconically tapering gain sections.

The or each gain section ideally tapers towards the distal end of the elongate solid shaft means.

Preferably, the elongate solid shaft means comprises at least one substantially cylindrical element.

Advantageously, the elongate solid shaft means comprises at least two said substantially cylindrical elements.

Ideally, the elongate solid shaft means comprises one more substantially cylindrical element than frustoconically tapering gain section.

The frustoconically tapering gain sections and the substantially cylindrical sections are preferably arranged alternatively along the elongate shaft means.

The portion of the elongate shaft means provided with the row or rows of recess means preferably comprises the or one of said substantially cylindrical elements.

A frustoconically tapering gain section may then be located immediately adjacent said portion at both a proximal and at a distal end thereof.

Preferably, each said frustoconically tapering gain section and each substantially cylindrical element extend coaxially with a single longitudinal axis in common.

In a first preferred embodiment, the operative head of the tool comprises a first operative head adapted to pierce hardened surgical cement when ultrasonically vibrated.

The first operative head is preferably adapted for operation urged distally into the cement.

Preferably, the first operative head comprises a substantially conical body extending coaxially from a distal end of the elongate shaft means, a tip of the conical body comprising a distal tip of the operative head.

Advantageously, the first operative head is provided with a plurality of channel means extending therethrough from its distal to its proximal face.

Said channel means may comprise cylindrical bores or passageways extending parallelly to the longitudinal axis of the tool and the operative head.

Alternatively, said channel means may comprise elongate groove means extending parallelly to the longitudinal axis of the tool and the operative head, each said groove means passing through a peripheral portion of the operative head so as to intersect with a widest circumference of the conical body.

The channel means thus provide a route for cement contacted and softened by an ultrasonically vibrated first operative head to flow through the operative head to a proximal face thereof for collection.

The channel means may extend proximally beyond the operative head into a distalmost portion of the elongate shaft means, thus forming further grooves extending proximally along the elongate shaft means.

Said further grooves may then guide softened cement further along the elongate shaft means to reduce accumulation of cement adjacent the operative head.

A distal tip of the conical body is preferably rounded.

This may obviate damage to bone contacted by the distal tip while the operative head is ultrasonically activated.

In a second preferred embodiment, the operative head of the tool comprises a second operative head adapted to collect softened surgical cement when ultrasonically vibrated.

The second operative head is preferably adapted for operation drawn proximally back through the cement.

Preferably, the second operative head comprises a substantially disc-shaped body located coaxially on a distal end of the elongate shaft means and extending radially therefrom at right angles to the longitudinal axis of the tool.

Advantageously, the disc-shaped body is provided on its proximal face with a plurality of elongate radial grooves.

Said radial grooves may have a part-cylindrical profile.

Softened cement contacted by said proximal face of the second operative head may thus be guided towards the elongate shaft means, around which it may be collected.

Preferably, a distal face of the disc-shaped body comprises a substantially planar disc.

Advantageously, a circumferential annular portion of the disc-shaped body may have a frustoconical profile, tapering slightly from a proximal to a distal edge thereof.

A bevelled annular portion may then extend between the distal edge of said circumferential portion and a circumference of the distal disc face.

An outermost end of each elongate radical groove on the proximal face of the disc-shaped body may then intersect with a proximal, widest, rim of the circumferential portion, producing a scalloped profile around said proximal rim.

Optionally, some or all of the elongate radial grooves may extend proximally along a distalmost portion of the elongate shaft means.

According to a second aspect of the present invention, there is provided a method for removal of surgical cement from within a lumen of a bone, including following extraction of a compromised implant from the lumen, comprising the steps of providing a surgical tool according to the first aspect of the present invention, applying an operative head of the surgical tool to solid surgical cement within the lumen and causing the operative head to vibrate ultrasonically in a mixed torsional/longitudinal mode, softening the cement for subsequent extraction.

According to a first embodiment of this second aspect, the surgical tool comprises a surgical tool according to the first embodiment of the first aspect of the present invention, which is applied by contacting the cement with a distal face of the operative head, causing the operative head to vibrate ultrasonically, and urging the operative head distally through the cement as it softens.

According to a second embodiment of this second aspect, the surgical tool comprises a surgical tool according to the second embodiment of the first aspect of the present invention, which is applied by contacting the cement with a peripheral portion of the proximal face of the operative head, causing the operative head to vibrate ultrasonically, and drawing the operative head proximally through the softened or softening cement.

Embodiments of the present invention will now be more particularly described by way of example and with reference to the Figures of the accompanying drawings, in which.

Figure 1A:
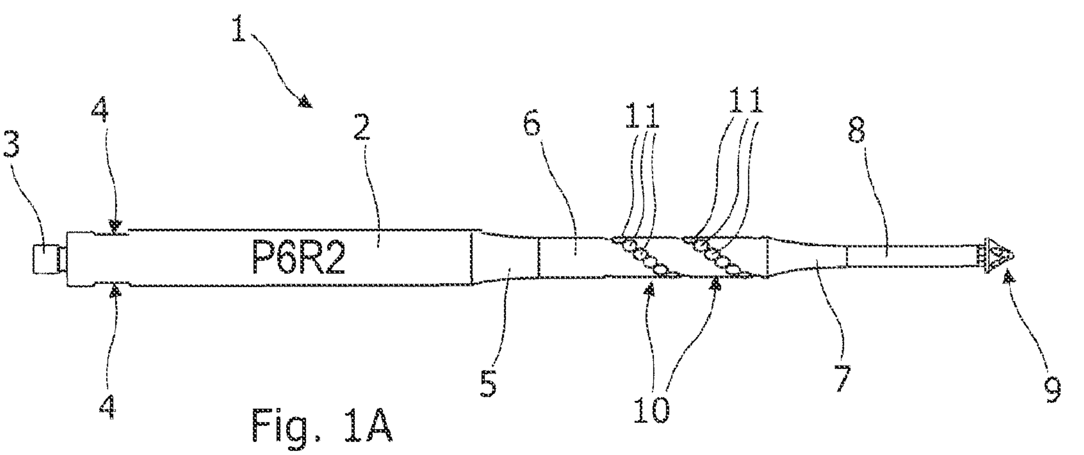
FIG. 1A is a side elevation of a first tool embodying the present invention, having a piercing operative head.

Referring now to the Figures, and to FIG. 1A in particular, a first, piercer probe 1 embodying the present invention is shown. The piercer probe 1 is formed from a single solid piece of titanium. It has an elongate form and (except where noted) is cylindrically symmetrical about a longitudinal axis extending between its proximal and distal ends.

An elongate proximal portion 2 of the piercer probe 1 is substantially cylindrical, with a proximal shoulder adjacent its proximal end, from which extends a threaded connector 3, by which the piercer probe 1 is operatively mountable to a source of longitudinal-mode ultrasonic vibrations, such as a transducer stack, usually via a conversion/amplification horn, as is known from the prior art (not shown). Adjacent the proximal shoulder is located an opposed pair of spanner flats 4, to assist with secure fastening of the threaded connector 3, such as to a cooperating threaded socket in a distal end of the horn.

At a distal end of the proximal portion 2, there extends a coaxially-aligned, elongate frustoconical first tapered gain feature 5, the function of which will be described below.

From a distal end of this first tapered gain feature 5, there extends an elongate cylindrical intermediate conversion portion 6 of the piercing probe 1, again coaxially aligned.

At a distal end of this intermediate conversion portion 6, there extends a coaxially-aligned elongate frustoconical second tapered gain feature 7, and at the distal end of this second tapered gain feature 7, there extends an elongate cylindrical distal portion 8 of the piercing probe 1 extends, once more coaxially-aligned.

At a distal end of the distal portion 8 of the piercing probe 1 is located a piercing head 9 of the probe 1. The piercing head 9 is of substantially conical form, aligned coaxially with a remainder of the piercing probe 1. The detailed structure of the piercing head 9 is described below, with reference to FIGS. 1B to 1D.

When the proximal threaded connector 3 of the piercing probe 1 is connected to a source of ultrasonic vibrations, which is then activated, the proximal 2, intermediate 6 and distal 8 portions of the piercing probe 1, together with the first 5 and second 7 tapered gain features linking them, thus act together as a elongate waveguide propagating ultrasonic vibrations to the distally-located piercing head 9.

The tapered gain features 5, 7 act to amplify these ultrasonic vibrations. The gain produced is inversely proportional to the reduction in cross-sectional area across the respective gain feature 5, 7 (in other words, there is an inverse square relationship between the gain and the reduction in diameter). This allows high amplitudes of ultrasonic vibrations to be delivered to the piercing head 9, without requiring an excessive signal strength from the source of ultrasonic vibrations. The particular arrangement shown also allows a relatively fine distal portion 8 and operative head 9 in combination with a robust proximal portion 2 for fastening to the vibrational source.

An additional feature of this piercing probe 1, however, which is characteristic of the present invention, is the presence of two helically-extending rows 10 of adjacent shallow circular dimples 11, which extend along and around the intermediate, conversion portion 6 of the piercing probe 1. These dimples 11 have a concave, dished profile, corresponding to a shallow portion of a spherical surface.

The function of the helically-extending rows 10 of dimples 11 is to cause a partial conversion of longitudinal-mode ultrasonic vibrations, transmitted from the proximal end of the piercer probe 1, into torsional-mode ultrasonic vibrations. The particular arrangement shown converts 20% of the vibrational energy to torsional mode. A mixed-mode ultrasonic vibration is hence delivered to the second tapered gain feature 7, the distal portion 8 and thence to the piercing head 9, with the proportion of longitudinal to torsional components being 4:1.

At present, it is believed that the degree of longitudinal-to torsional-mode conversion may depend on the depth of the dimples 11, their relative diameters, their separations from adjacent dimples 11 in the same row 10, the lengths of the rows 10 relative to that of the intermediate conversion portion 6, and the spacing between rows 10, although there may be other factors as yet unidentified. It is believed that variations of these parameters could allow probes to be designed to select the degree of conversion from longitudinal to torsional modes.

The benefits of the combined longitudinal/torsional mode vibrations, when imposed on the piercing head 9, will be described below.

Figure 1B:
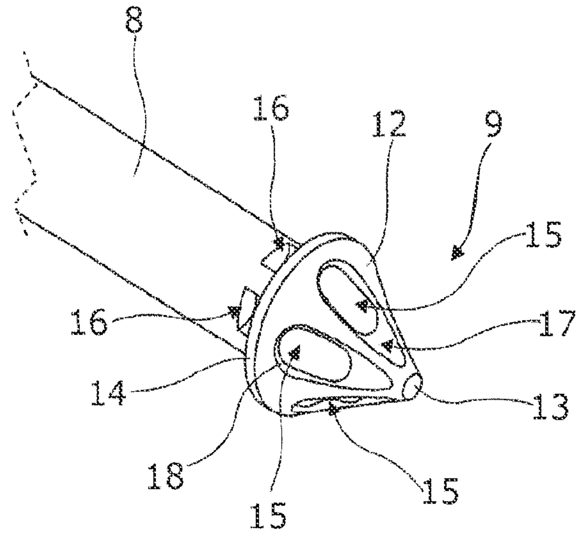
FIG. 1B is a scrap isometric view of the piercing operative head of the tool of FIG. 1A.
Figure 1C:
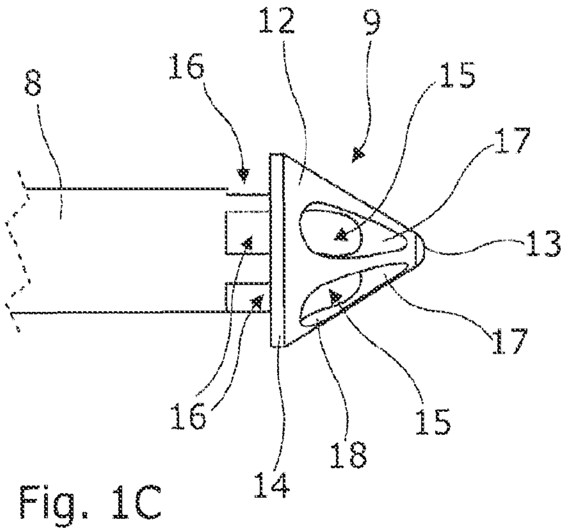
FIG. 1C is a scrap side elevation of the piercing operative head of FIG. 1B.
Figure 1D:
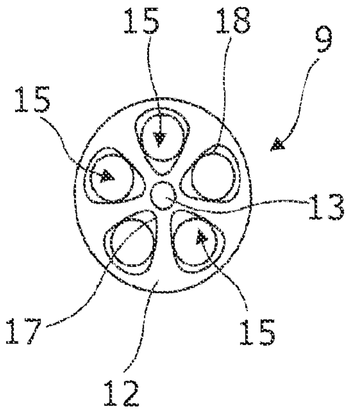
FIG. 1D is a distal end elevation of the piercing operative head of FIG. 1B.

Referring to FIGS. 1B, 1C and 1D, the piercing head 9 is shown in more detail. The head 9 comprises a straight-sided cone 12 with a radiused distal tip 13 and a short cylindrical section 14 extending proximally from the wider, proximal end of the cone 12. In this case, the cone 12 is approximately an equilateral triangle in cross-section (see FIG. 1C), and has a maximum width slightly less than 50% greater than a diameter of the distal portion 8 of the waveguide. Other examples of the piercer probe (not shown) have generally the same cone 12 proportions, but different overall cone 12 dimensions.

In this example, five cylindrical holes 15 have been bored through from an angled distal face of the cone 12 to a flat proximal face of the short cylindrical section 14 of the head 9. Each hole has a bore extending parallel to the joint longitudinal axis of the waveguide 2,5,6,7,8 and the cone 12, The arrangement of these holes 15, equally spaced around the head 9, is best shown in FIG. 1D. The holes 15 also extend proximally of the piercing head 9, forming short longitudinal grooves 16 in the distal portion 8 of the waveguide 2,5,6,7,8.

Each of the holes 15 is opened out slightly where it emerges from the angled distal surface of the cone 12. A first bevelled surface 17 extends from an inner, distal edge of each holes 15, tapering the hole 15 inwardly towards the distal tip 13 of the cone 12. A second bevelled surface 18 extends from an outer, proximal edge of each hole 15, such that these bevelled surfaces 17,18 between them open up the distal end of each otherwise cylindrical hole 15 into a funnel shape.

Other sizes of piercing head 9 are provided with different numbers of such holes 15, all still extending longitudinally right through the cone 12 and the proximal section 14. The smallest sizes of piercing head 9 instead have part-cylindrical-section grooves machined longitudinally through circumferential zones of the cone 12 and proximal section 14 (effectively, these grooves comprise cylindrical holes 15 of sufficient diameter to breach the circumference of the cone 12 and proximal section 14; they may still have the first bevelled surface 17 extending from the distal inner edge of each groove).

The operation of the piercing head 9 is believed to proceed as follows. Longitudinal mode ultrasonic vibrations are applied to the proximal end of the probe 1, and are partially converted to torsional mode in the intermediate portion 6 of the probe 1. The cone 12 of the piercing head 9 is brought into contact with solid cement within the lumen of the bone, and these ultrasonic vibrations are transmitted into the cement, softening it and allowing the piercing head 9 to be driven distally to penetrate further into the cement. With the piercing head 9 vibrating both longitudinally and torsionally, the ultrasonic vibrational energy is transmitted efficiently into the cement. The lower proportion of longitudinal mode in the vibrations means that the effective longitudinal displacement for a given vibrational energy is lower than for traditional apparatus and so the risk of damaging the bone wall by projecting vibrations distally into the bone is reduced. The torsional mode component, meanwhile, is transmitted efficiently into the adjacent cement rather then being transmitted a significant distance from the head 9.

As the vibrated piercing head 9 is pushed into the softened cement, the cement is channelled by the surfaces 17, 18 into the longitudinally-extending holes 15 through the head 9. The softened cement thus passes through the piercing head 9 to its proximal face and to the longitudinal grooves 16 in the distal portion 8 of the waveguide 2,5,6,7,8. It is found that the use of a proportion of torsional mode vibrations modifies the flow of the softened cement through the piercing head 9 and proximally along the distal portion 8. The result is that when the cement begins to set again, it forms a less compact "sleeve" around the distal portion 8 than it does when only longitudinal-mode vibrations are present. This makes it significantly easier to clean this re-hardened cement from the piercing probe 1 between uses than it is for current probes, cleaning the re-set cement from the head and shaft of conventional probes can be a significant inconvenience.

The piercing head 9 is mainly used to pierce and break up bulk volumes of hardened cement, including the distal plug of cement that is used to block the lumen of the bone, distally of the {former} position of the implant.

Once the bulk cement has been broken up with the piercing probe 9, it is usually found to be more effective to remove the remainder of the cement with an ultrasonically-vibratable scraping probe, used by moving its operative head to a position distal of the cement and withdrawing the ultrasonically vibrating probe back through the cement, softening it and scraping and scooping up the softened cement. This allows the rest of the bulk cement to be removed from adjacent the gaps left by the piercing probe 1, and allows residual cement to be scraped off the walls of the bone.

Figure 2A:
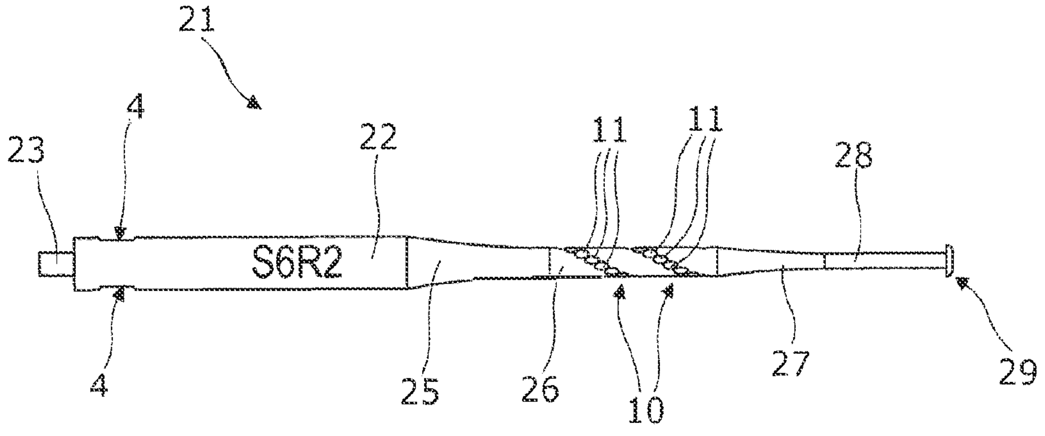
FIG. 2A is a side elevation of a second tool embodying the present invention, having a scraping operative head.

FIGS. 2A shows a second scraper probe 21 embodying the present invention, to be used for this step of the procedure. As with the piercer probe 1, the scraper probe 21 is made from a single solid piece of titanium, and has an elongate form with cylindrical symmetry about its longitudinal axis, except where noted below.

The main structure of the scraper probe 21 is similar to that of the piercer probe 1, although the proportions are different. There is thus an elongate proximal portion 22, which is substantially cylindrical, with a threaded connector 23 extending from its proximal end, by which the probe 21 is operatively mountable to a transducer stack of conventional form provided with a conversion/amplification horn as in the prior art (not shown). Adjacent a proximal shoulder of the proximal portion 22 is located an opposed pair of spanner flats 24, corresponding to those 4 of the piercer probe 1.

A coaxially-aligned elongate frustoconical first tapered gain feature 25 extends from a distal end of the proximal portion 22, and an elongate cylindrical intermediate, conversion portion 26 extends coaxially from a distal end of the first tapered gain feature 25. A second elongate frustoconical tapered gain feature 27 extends coaxially from a distal end of the intermediate portion 26, and an elongate cylindrical distal portion 28 of the scraper probe 21 extends coaxially from a distal end of the second tapered gain feature 27. As with the piercer probe 1, the proximal portion 22, first tapered gain feature 25, intermediate portion 26, second tapered gain feature 27 and distal portion 28 of the scraper probe 21 extend coaxially along the longitudinal axis of the probe 21 as a whole.

At a distal end of the distal portion 28 is located a scraping head 29 of generally discoidal form, again aligned coaxially with a remainder of the scraper probe 21. The structure and function of the scraping head 29 will be described below, with reference to FIGS. 2B to 2D.

Thus, when the proximal threaded connector 23 is connected to the source of ultrasonic vibrations, and this is activated, the proximal 22, intermediate 26 and distal 28 portions of the probe 21, together with the first 25 and second 27 tapered gain features act as a waveguide transmitting ultrasonic vibrations to the scraping head 29. The tapered gain features 25, 27 have the same functions as the corresponding tapered gain features 5, 7 of the piercer probe 1.

Also, as with the piercer probe 1 of the FIG. 1A, the scraping probe 21 of FIG. 2A is provided with two helically-extending rows 10 of adjacent shallow circular dimples 11, extending along and around its intermediate, conversion portion 26. The function of the rows 10 of dimples 11 is once more to cause a partial conversion of longitudinal-mode ultrasonic vibrations to torsional-mode ultrasonic vibrations. The arrangement shown produces about a 20% conversion, such that mixed-mode ultrasonic vibrations are propagated through to the scraping head 29, again with a proportion of longitudinal to torsional mode components of 4.1.

Figure 2B:
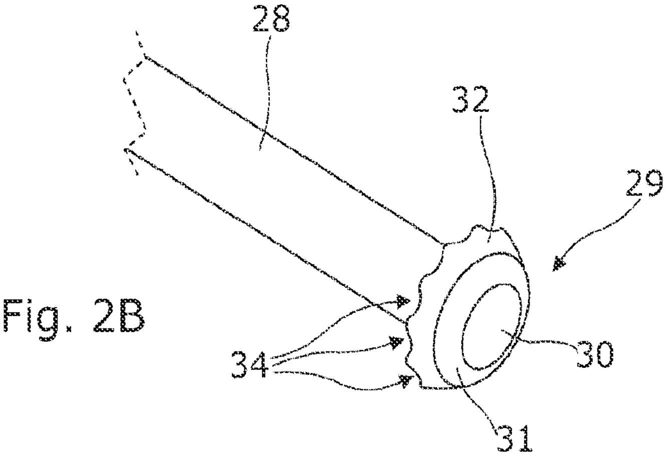
FIG. 2B is a scrap isometric view of the scraping operative head of the tool of FIG. 2A.
Figure 2C:
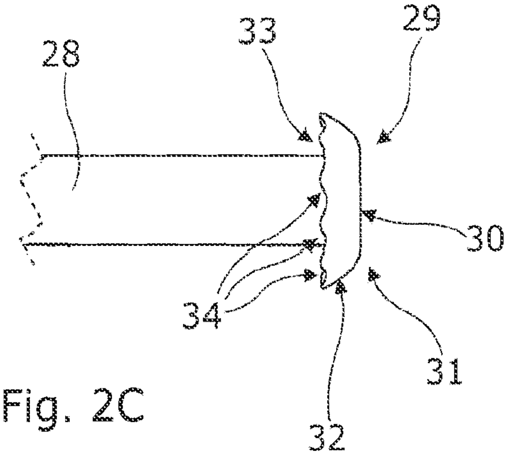
FIG. 2C is a scrap side elevation of the scraping operative head of FIG. 2B.
Figure 2D:
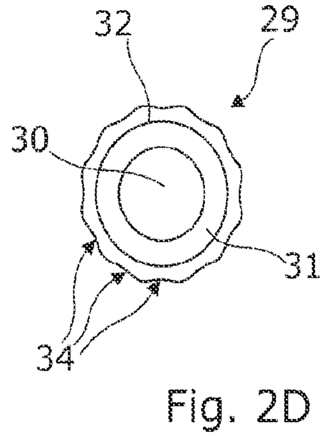
FIG. 2D is a distal end elevation of the scraping operative head of FIG. 2B.

Referring now to FIGS. 2B, 2C and 2D, the scraping head 29 is shown in more detail. The head 29 is generally discoidal. A distal surface 30 of the head 29 comprises a flat disc, aligned orthogonally to the longitudinal axis of the probe 21. A periphery of the scraping head 29 comprises a narrow, tapered zone 32, tapering distally and expanding proximally, connected to the distal disc 30 by an annular radiused zone 31, which effectively blends the profile of the disc 30 into the profile of the tapered zone 32. A proximal face 33 of the scraping head 29 is provided with a series of radially-extending grooves (not visible in these Figures), which extend outwardly from the distal portion 28 of the probe 21, passing out through a periphery of the tapered zone 32 of the scraping head 29, thus forming a series of scallops 34 around a periphery of the head 29.

These concave grooves on the proximal face 33 act to focus ultrasonic vibrations on cement brought into contact with the proximal face 33, particularly when mixed-mode ultrasonic vibrations with a torsional component are used. Thus, when the scraping head 29 is drawn proximally through hardened cement, the cement is rapidly softened when it approaches and contacts the ultrasonically-vibrated proximal face 33.

The grooves also help guide the softened cement away from the proximal face 33 and up to the distal portion 28 of the probe 21. Again, with the presence of torsional mode vibrations, the softened cement sets again in a "sleeve" surrounding the distal portion 28, which is found to be more loosely anchored in place than when pure longitudinal mode vibrations are used, and is hence much easier to remove from the scraper probe 21 between uses.

Thus, this scraper probe 21 can be used to debulk and clean up residual cement in a second stage of the cement removal procedure, more rapidly and effectively than for existing longitudinally-vibratable tools.

Figure 3A:
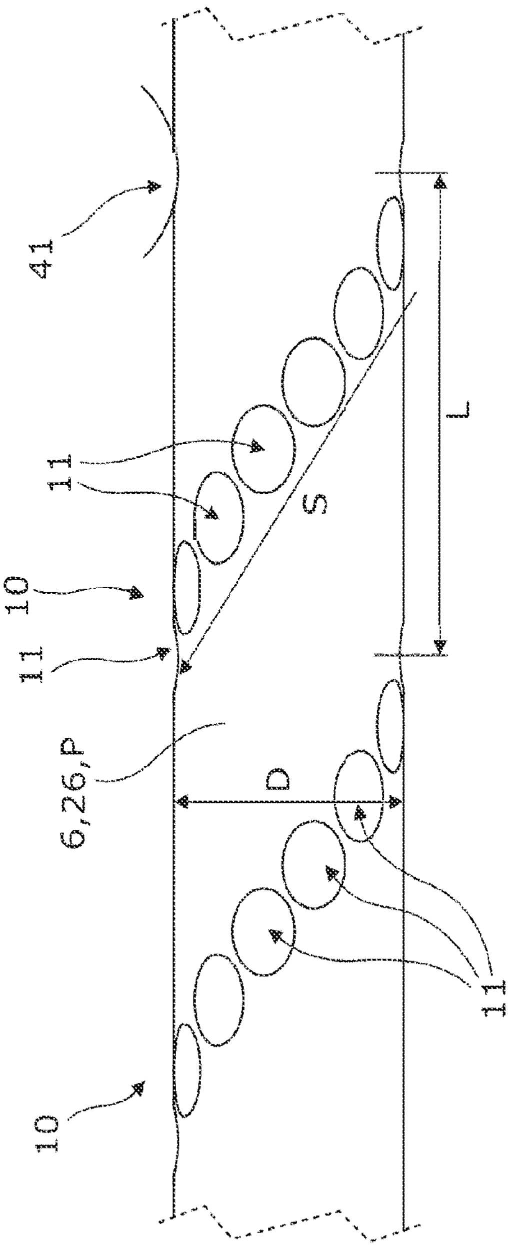
FIG. 3A is a scrap side elevation of a elongate cylindrical intermediate conversion portion of the tool of FIG. 1A or the tool of FIG. 2A.
Figure 3B:
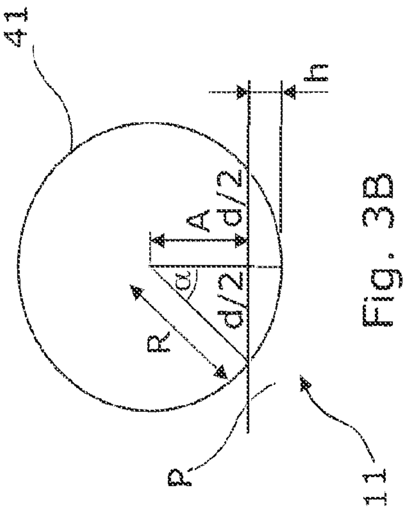
FIG. 3B is a schematic side elevation of a dimple of the elongate cylindrical intermediate conversion portion of FIG. 3A, showing details of its geometry.

FIGS. 3A and 3B show in more detail how the helical strings or rows 10 of dimples 11 in the tools of the present invention differ from the known helical strings of recesses perforating the wall of a hollow waveguide in the known systems that produce a total conversion of longitudinal mode ultrasonic vibrations, input from a conventional Langevin transducer to a proximal end of the tool, to torsional mode ultrasonic vibrations, at the operative distal end of the tool.

For various reasons, such a total conversion to torsional mode vibrations has been found to be unsatisfactory in use. As noted above, a partial conversion of input longitudinal mode vibrations to torsional mode has been found to provide improved overall performance in the removal of PMMA cement during revision arthroplasty.

It has been found that the torsional stiffness of an elongate cylindrical probe 1, 21 can be modified suitably by the formation of helical strings 10 of shallow recesses/dimples 11 having a part-spherical profile formed by cutting with a ball-noted cutting tool into the cylindrical surface of an elongate cylindrical portion 6,26 of the waveguide of the tool 1,21. When these shallow dimples 11 are used instead of deep penetrating bores, they can conveniently be configured to convert a desired proportion of longitudinal mode displacements input at a proximal end of a tool 1,21 to torsional mode displacements in the respective operative distal effector 9,29. Significant increases in probe 1,21 performance have been observed when longitudinal/torsional (L/T) ratios of up to 4/1 have been generated at the output/effector 9,29 of either piercer 1 or scraper 21 probes.

Referring to FIGS. 3A and 3B once more, the relationships between system parameters which affect the conversion amplitude are shown. In summary:

(i) R=radius of ball-nosed cutter 41 used to create dimples 11

(ii) P=probe shaft 6,26 into which helical strings 10 of dimples 11 cut (iii) h=dimple depth (iv) A=distance from centre of cutter 41 to line of intersection of dimple 11 with cylindrical probe surface (v) d=dimple diameter at intersection with cylindrical probe surface (vi) D=probe P shaft diameter (vii) α=angle between cutter 41 radius and line dissecting dimple diameter (viii) S=half the helical length of the string 10 of dimples 11 lying in peripheral probe P surface (ix) L=linear projection of string 10 of dimples 11 along probe P surface, parallel to axis of elongate cylindrical probe P (x) C=circumference of waveguide/probe P=πD/2

The following equations link the above variables, allowing definitive control of dimple 11 characteristics:

$$A=R-h \tag{1}$$

$$\sin \alpha=d/2R \tag{2}$$

$$S=[L^2+(D\pi/2)^2]^{1/2} \tag{3}$$

In the particular example illustrated in FIG. 3A, there are two superposed helical strings 10 of dimples 11 aligned at opposing points around the circumference of the probe, each extending 360° around the cylindrical surface of the probe.

Probe P has diameter D=7.6 mm.

Minimum distance between diametrically opposed dimples (shown as D1)=6.91 mm.

Dimple depth, h=(D−D1)/2=0.345 mm.

Cutter 41 ball diameter=6.0 mm, radius R=3.0 mm

Using the dimple geometry shown in FIG. 3A/3B allows determination of dimple features, viz:

$$A=R-h=2.655 \text{ mm}$$

$$\cos \alpha=A/R=0.885$$

α=27.75° sin α=0.4656

$$d=\sin \alpha\times 2R=2.8 \text{ mm}$$

$$d/2=1.4 \text{ mm}$$

$$C=\pi D/2=11.94 \text{ mm}$$

$$S=[L^2+C^2]^{1/2} \text{ so } S=19.14 \text{ mm with } L \text{ here 15 mm}$$

These values allow seven complete dimples in a half-circumference of the probe, with a total overlap of 0.139

The invention claimed is:

1. An ultrasonically-vibratable surgical tool adapted for cement removal in revision arthroplasty, comprising elongate solid shaft means, mountable at a proximal end to a source of longitudinal-mode ultrasonic vibrations, so as to act as a waveguide for propagation of said ultrasonic vibrations, and having located adjacent a distal end of the elongate solid shaft means an operative head adapted to act on the cement, wherein a portion of the elongate solid shaft means intermediate between said proximal and distal ends comprises at least one row of dimples extending helically along and around said portion of the elongate solid shaft means, with each said dimple being separate from each adjacent said dimple, such that said longitudinal-mode ultrasonic vibrations are at least partially converted to torsional-mode ultrasonic vibrations.

2. The ultrasonically-vibratable surgical tool as claimed in claim 1, wherein each dimple extends into the elongate solid shaft means to a depth of less than half of a maximum width of the dimple.

3. The ultrasonically-vibratable surgical tool as claimed in claim 1, wherein each dimple extends into the elongate solid shaft means to a depth of less than a quarter of the maximum width of the dimple.

4. The ultrasonically-vibratable surgical tool as claimed in claim 1, wherein each dimple is identical to each other dimple.

5. The ultrasonically-vibratable surgical tool as claimed in claim 1, wherein each dimple comprises a circular dimple.

6. The ultrasonically-vibratable surgical tool as claimed in claim 5, wherein each circular dimple has a part-spherical profile.

7. The ultrasonically-vibratable surgical tool as claimed in claim 1, wherein the or each of the at least one row of dimples extends for less than an overall length of the portion of the elongate solid shaft means.

8. The ultrasonically-vibratable surgical tool as claimed in claim 1, wherein the or each of the at least one row of dimples extends for more than half of the overall length of the portion of the elongate solid shaft means.

9. The ultrasonically-vibratable surgical tool as claimed in claim 1, comprising at least two rows of dimples.

10. The ultrasonically-vibratable surgical tool as claimed in claim 9, wherein each row of dimples is substantially identical to each other row of dimples.

11. The ultrasonically-vibratable surgical tool as claimed in claim 9, wherein each row of said at least two rows of dimples are spaced from each adjacent row thereof by a separation of at least twice a maximum diameter of the dimples.

12. The ultrasonically-vibratable surgical tool as claimed in claim 1, wherein the elongate solid shaft means of the tool comprises:

an intermediate conversion portion upon which the at least one row of dimples extend helically along and around;

a first tapered gain feature positioned adjacent a proximal end of the intermediate conversion portion; and a second tapered gain feature positioned adjacent a distal end of the intermediate conversion portion.

13. The ultrasonically-vibratable surgical tool as claimed in claim 1, wherein the elongate solid shaft means comprises at least one substantially cylindrical element.

14. The ultrasonically-vibratable surgical tool as claimed in claim 1, wherein an operative head of the tool comprises a first operative head adapted to pierce hardened surgical cement when ultrasonically vibrated.

15. The ultrasonically-vibratable surgical tool as claimed in claim 14, wherein the first operative head comprises a substantially conical body extending coaxially from a distal end of the elongate shaft means, a tip of the conical body comprising a distal tip of the first operative head.

16. The ultrasonically-vibratable surgical tool as claimed in claim 14, wherein the first operative head is provided with a plurality of channel means extending through the first operative head from its distal face to its proximal face.

17. The ultrasonically-vibratable surgical tool as claimed in claim 1, wherein an operative head of the tool comprises an operative head adapted to collect softened surgical cement when ultrasonically vibrated.

18. The ultrasonically-vibratable surgical tool as claimed in claim 17, wherein the operative head comprises a substantially disc-shaped body located coaxially on a distal end of the elongate solid shaft means and extending radially from the elongate solid shaft means at right angles to a longitudinal axis of the tool.

19. The ultrasonically-vibratable surgical tool as claimed in claim 18, wherein a proximal face of the disc-shaped body comprises a plurality of elongate radial grooves.

20. A method for removal of surgical cement from within a lumen of a bone, including after extraction of a compromised implant from the lumen, comprising the steps of providing a surgical tool as claimed in claim 1, applying an operative head of the surgical tool to solid surgical cement within the lumen and causing the operative head to vibrate ultrasonically in a mixed torsional/longitudinal mode, softening the cement for subsequent extraction.

21. An ultrasonically-vibratable surgical tool adapted for cement removal in revision arthroplasty, comprising elongate solid shaft means, mountable at a proximal end to a source of longitudinal-mode ultrasonic vibrations, so as to act as a waveguide for propagation of said ultrasonic vibrations, and having located adjacent a distal end of the shaft means an operative head adapted to act on the cement, wherein a portion of the elongate shaft means intermediate between said proximal and distal ends is provided with at least one row of recess means extending helically along and around said portion of the elongate shaft means, with each said recess means being separate from each adjacent said recess means, such that said longitudinal-mode ultrasonic vibrations are at least partially converted to torsional-mode ultrasonic vibrations;

wherein the operative head of the tool comprises a second operative head adapted to collect softened surgical cement when ultrasonically vibrated; and wherein the second operative head comprises a substantially disc-shaped body located coaxially on a distal end of the elongate shaft means and extending radially from the elongate shaft means at right angles to the longitudinal axis of the tool.

22. The ultrasonically-vibratable surgical tool as claimed in claim 21, wherein the disc-shaped body is provided on its proximal face with a plurality of elongate radial grooves.

* * * * *